(12) United States Patent
Tachibana (10) Patent No.: US 7,789,868 B2
(45) Date of Patent: Sep. 7, 2010

(54) WORN ARTICLE AND METHOD FOR PRODUCING THE SAME

(75) Inventor: Ikuo Tachibana, Osaka (JP)

(73) Assignee: Zuiko Corporation, Osaka (JP)

( * ) Notice: Subject to any disclaimer, the term of this patent is extended or adjusted under 35 U.S.C. 154(b) by 584 days.

(21) Appl. No.: 10/596,258

(22) PCT Filed: Dec. 22, 2004

(86) PCT No.: PCT/JP2004/019175

§ 371 (c)(1),
(2), (4) Date: Jun. 7, 2006

(87) PCT Pub. No.: WO2005/060908

PCT Pub. Date: Jul. 7, 2005

(65) Prior Publication Data

US 2009/0018520 A1    Jan. 15, 2009

(30) Foreign Application Priority Data

Dec. 24, 2003  (JP)  ............................. 2003-426048

(51) Int. Cl.
*A61F 13/20* (2006.01)
(52) U.S. Cl. ................................................. 604/385.23
(58) Field of Classification Search ......... 604/386–391, 604/393–395, 402, 385.23
See application file for complete search history.

(56) References Cited

U.S. PATENT DOCUMENTS

| | | | | |
|---|---|---|---|---|
| 1,977,604 A | * | 10/1934 | Alsop | 604/394 |
| 4,022,212 A | * | 5/1977 | Lovison | 604/395 |
| 4,892,598 A | * | 1/1990 | Stevens et al. | 156/91 |
| 5,069,672 A | * | 12/1991 | Wippler et al. | 604/385.14 |
| 5,187,817 A | * | 2/1993 | Zolner | 2/400 |
| 5,725,518 A | | 3/1998 | Coates | |
| 5,772,649 A | * | 6/1998 | Siudzinski | 604/386 |
| 6,605,071 B1 | * | 8/2003 | Gray et al. | 604/385.28 |

(Continued)

FOREIGN PATENT DOCUMENTS

EP    763353 A2 *  3/1997

(Continued)

OTHER PUBLICATIONS

International Search Report for corresponding Application No. PCT/JP2004/019175 mailed Mar. 22, 2005.

(Continued)

*Primary Examiner*—Tatyana Zalukaeva
*Assistant Examiner*—Benedict L Hanrahan
(74) *Attorney, Agent, or Firm*—Renner, Otto, Boisselle & Sklar, LLP (57) ABSTRACT

A worn article includes a fitting portion 1 that fits around a torso of a wearer, and an absorbent portion 2 covering a crotch of the wearer and absorbing body fluid from the wearer. The absorbent portion 2 includes a first end portion 23 and a second end portion 24 that are connected to the fitting portion 1. The first end portion 23 of the absorbent portion 2 can be detached from the fitting portion 1. A cover sheet 4 is provided covering at least a portion of the first end portion 23. A portion of the cover sheet 4 is processed so that the cover sheet 4 is tearable.

9 Claims, 10 Drawing Sheets

U.S. PATENT DOCUMENTS

| | | | |
|---|---|---|---|
| 6,752,797 B2* | 6/2004 | Oba | 604/395 |
| 7,393,429 B2* | 7/2008 | Tachibana | 156/256 |
| 2001/0023344 A1* | 9/2001 | Oba | 604/395 |
| 2006/0052763 A1* | 3/2006 | Tachibana | 604/395 |
| 2006/0259001 A1* | 11/2006 | Roehrl et al. | 604/385.11 |

FOREIGN PATENT DOCUMENTS

| | | |
|---|---|---|
| EP | 0 763 353 A3 | 10/1998 |
| EP | 0 985 398 A2 | 3/2000 |
| JP | 09-075390 | 3/1997 |
| JP | 2003-520627 | 7/2003 |
| JP | 2003-526406 | 9/2003 |
| JP | 2003-527152 | 9/2003 |
| JP | 2003-527153 | 9/2003 |
| JP | 2003-528649 | 9/2003 |
| JP | 2003-528650 | 9/2003 |
| JP | 2003-529398 | 10/2003 |
| JP | 2003-529399 | 10/2003 |
| JP | 2003-529400 | 10/2003 |
| JP | 2003-530904 | 10/2003 |
| WO | 01/13843 | 3/2001 |
| WO | 01/13844 | 3/2001 |
| WO | 01/13845 | 3/2001 |
| WO | 01/13846 | 3/2001 |
| WO | 01/13847 | 3/2001 |
| WO | 01/13848 | 3/2001 |
| WO | 01/13849 | 3/2001 |
| WO | 01/13850 | 3/2001 |
| WO | 01/13851 | 3/2001 |
| WO | 01/13852 | 3/2001 |
| WO | 02/32363 A2 | 4/2002 |
| WO | 02/076361 A1 | 10/2002 |

OTHER PUBLICATIONS

Supplementary European Search Report for corresponding European Application No. EP 04 080 7532 dated Apr. 16, 2010.

* cited by examiner

WORN ARTICLE AND METHOD FOR PRODUCING THE SAME

TECHNICAL FIELD

The present invention relates to worn articles such as disposable pants and disposable diapers, and method for producing the same.

BACKGROUND ART

The following patent documents disclose refastenable absorbent articles. These patent documents fail to disclose a cover sheet for covering a connecting portion.

The first patent document: Japanese National Phase PCT Laid-Open Publication No. 2003-520627 (abstract)

The second patent document: Japanese National Phase PCT Laid-Open Publication No. 2003-526406 (abstract)

The third patent document: Japanese National Phase PCT Laid-Open Publication No. 2003-527153 (abstract)

The fourth patent document: Japanese National Phase PCT Laid-Open Publication No. 2003-529398 (abstract)

The fifth patent document: Japanese National Phase PCT Laid-Open Publication No. 2003-529399 (abstract)

The sixth patent document: Japanese National Phase PCT Laid-Open Publication No. 2003-530904 (abstract)

The seventh patent document: Japanese National Phase PCT Laid-Open Publication No. 2003-527152 (abstract)

The eighth patent document: Japanese National Phase PCT Laid-Open Publication No. 2003-528649 (abstract)

The ninth patent document: Japanese National Phase PCT Laid-Open Publication No. 2003-528650 (abstract)

The tenth patent document: Japanese National Phase PCT Laid-Open Publication No. 2003-529400 (abstract)

DISCLOSURE OF THE INVENTION

An object of the present invention is to cover a detachable portion and to thereby prevent an absorbent portion from inadvertently coming off a fitting portion.

In order to achieve the object, a worn article of the present invention includes a fitting portion that fits around a torso of a wearer, and an absorbent portion covering a crotch of the wearer and absorbing body fluid from the wearer. The absorbent portion includes a first end portion and a second end portion that are connected to the fitting portion. The first end portion of the absorbent portion can be detached from the fitting portion. A cover sheet is provided covering at least a portion of the first end portion.

In this way, the portion corresponding to the first end portion that can be detached from the fitting portion is covered and protected by the cover sheet, whereby it is possible to prevent the first end portion from inadvertently coming off.

In the present invention, it is preferred that a portion of the cover sheet is processed so that the cover sheet is tearable, and the detachable member is placed on the absorbent portion or the fitting portion in the vicinity of the processed portion of the cover sheet.

As the cover sheet is processed so that the cover sheet is tearable, the cover sheet can be easily torn.

In one aspect of the present invention, the fitting portion includes an abdominal-side portion covering an abdominal side of the wearer, and a back-side portion covering a back side of the wearer. The first end portion of the absorbent portion is connected to the abdominal-side portion of the fitting portion, and the second end portion of the absorbent portion is connected to the back-side portion of the fitting portion. The first end portion is detachably touch-fastened to the fitting portion, and a portion of the cover sheet that is covering the first end portion or a vicinity thereof is formed to be tearable.

In this way, it is possible to check the soiling of the absorbent portion after the article is worn, by breaking a portion of the cover sheet to expose the first end portion and then peeling the absorbent portion off the fitting portion. Moreover, it is possible to disconnect the absorbent portion and the fitting portion from each other, and replace a portion of the absorbent portion. Then, as necessary, it is possible to connect the absorbent portion and the fitting portion to each other, and to refasten the worn article.

A tearable portion may be formed in the cover sheet, the tearable portion being processed so that the cover sheet is tearable, so that at least a portion of the first end portion will be exposed when the cover sheet is torn along the tearable portion.

More preferably, in the touch-fastened first end portion, an inner surface of the absorbent portion is facing an outer surface of the abdominal-side portion of the fitting portion, and an inner surface of the cover sheet is facing an outer surface of the absorbent portion, and the fitting portion, the absorbent body and the cover sheet are layered in this order starting from an inner side in a position corresponding to the first end portion.

BRIEF DESCRIPTION OF THE DRAWINGS

FIGS. 1(a) and 1(b) are schematic perspective views showing a worn article of the first embodiment of the present invention, FIG. 1(a) shows the cover sheet to be torn, and FIG. 1(b) shows the torn cover sheet.

DESCRIPTION OF THE REFERENCE NUMERALS

1: Fitting portion
1F: Abdominal-side portion
1B: Back-side portion

2: Absorbent portion
23: First end portion
24: Second end portion
3: Fastener member
4: Cover sheet
41: Tearable portion

BEST MODE FOR CARRYING OUT THE INVENTION

The present invention will be understood more clearly from the following description of preferred embodiments taken in conjunction with the accompanying drawings. However, it will be appreciated that the embodiments and the drawings are given for the purpose of mere illustration and explanation and that the scope of the present invention is to be defined by the appended claims. In the accompanying drawings, the same reference numerals denote the same or corresponding elements throughout several figures.

First Embodiment

Embodiments of the present invention will now be described with reference to the drawings.

Figure 1A:
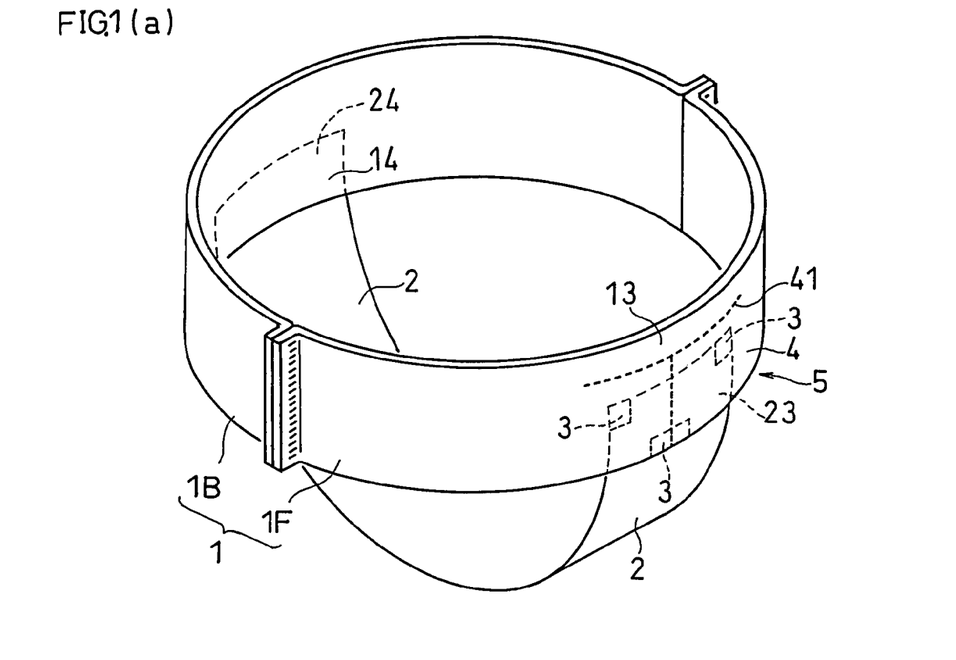
Figure 1B:
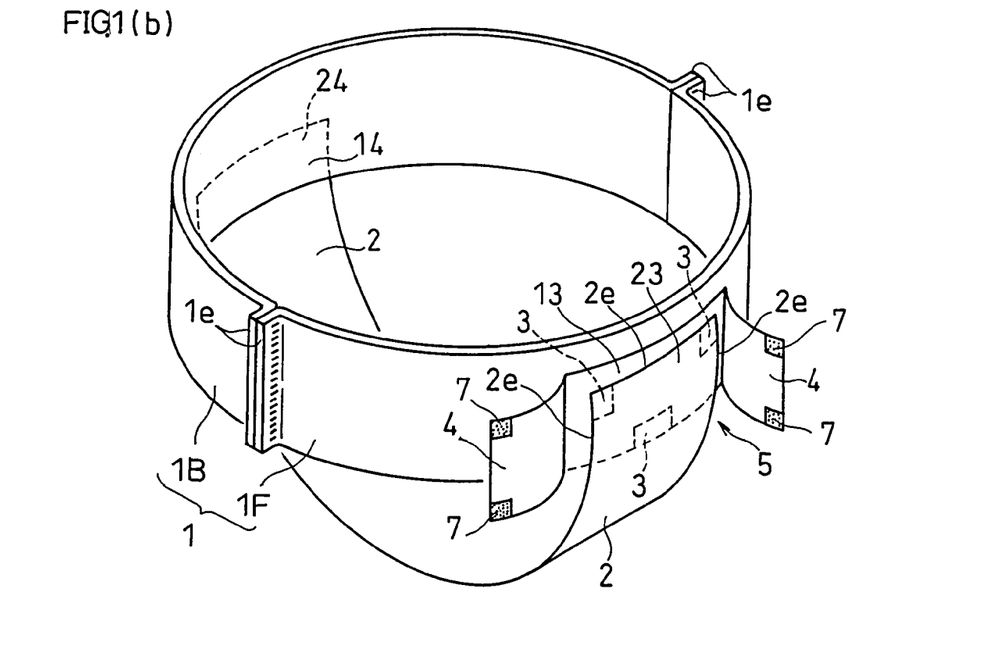

As shown in FIG. 1, a worn article of the present embodiment includes a fitting portion 1 that fastens around the torso of the wearer, and an absorbent portion 2 for absorbing body fluid of the wearer.

Figure 2A:
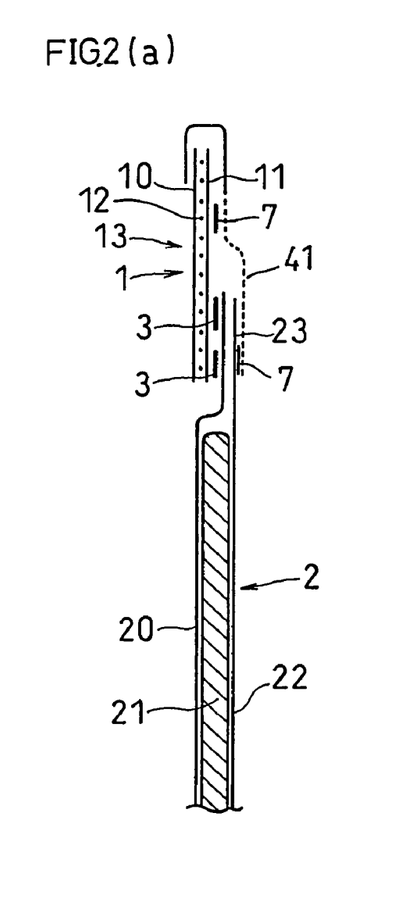
FIG. 2(a) is a schematic cross-sectional view showing an important part of the first embodiment.
Figure 2B:
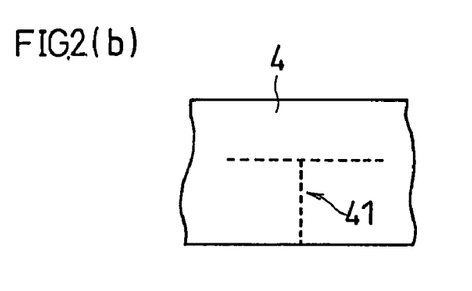
FIGS. 2(b), 2(c) and 2(d) are plan views each showing an example of the tearable portion.
Figure 2C:
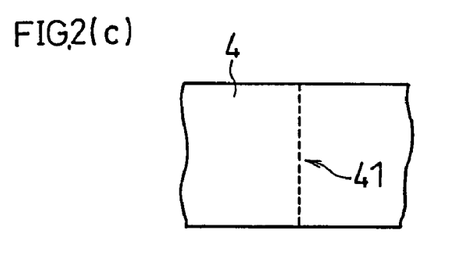
Figure 2D:
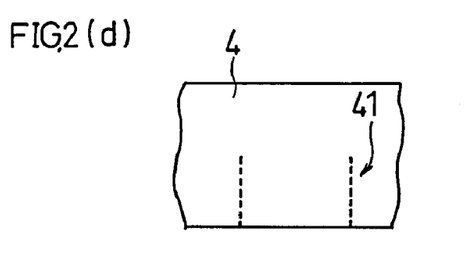

As shown in FIG. 2(a), the fitting portion 1 includes elastic members 12 sandwiched between at least two sheets of nonwoven fabric 10 and 11. The elastic member 12 may be a thread rubber, a flat rubber, a scrim, an elastic hot-melt resin, a film, a urethane foam, etc. The fitting portion 1 includes an abdominal-side portion 1F covering the abdominal side of the wearer, and a back-side portion 1B covering the back side of the wearer.

Figure 6A:
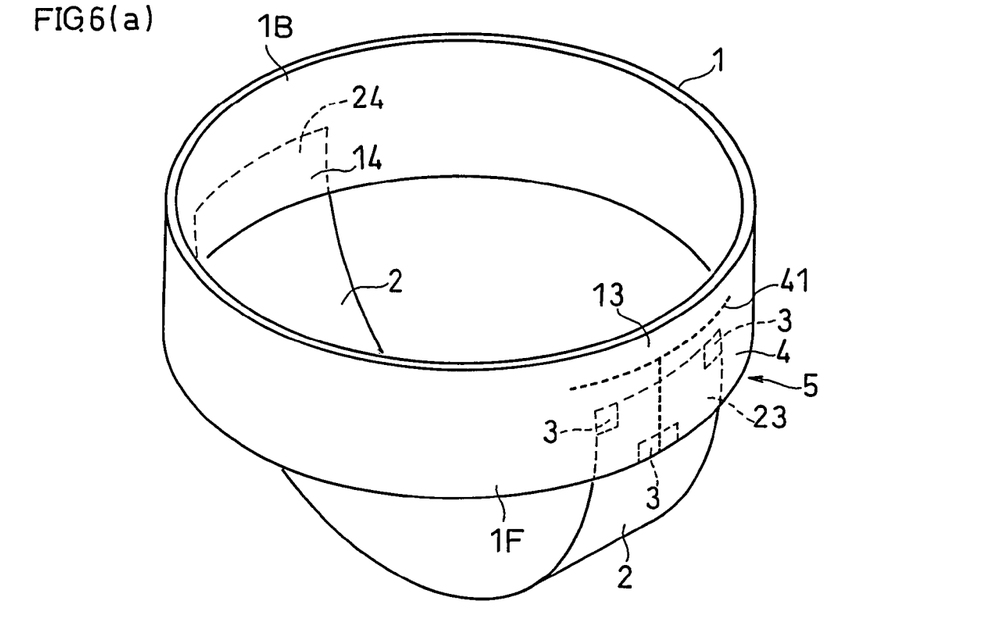
FIG. 6(a) is a schematic perspective view showing the worn article before tearing the cover sheet according to a variation of the invention.
Figure 6B:
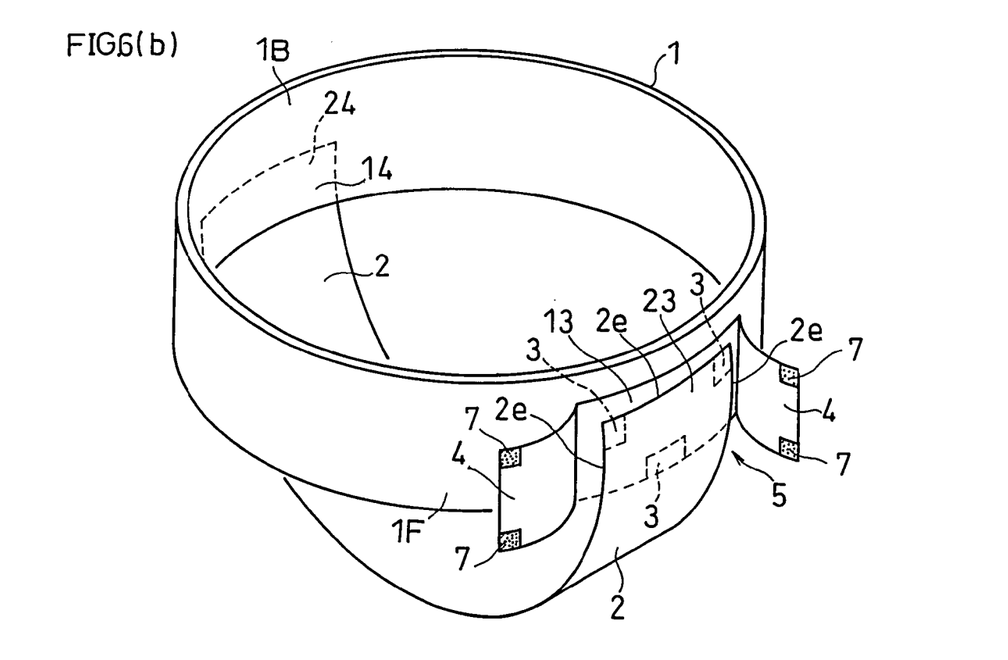
FIG. 6(b) is a schematic perspective view showing the worn article after tearing the cover sheet.

For example, as shown in FIG. 1(a), the abdominal-side portion 1F and the back-side portion 1B may be separately produced with the elastic member 12 sandwiched therein, and end portions 1e and 1e of the abdominal-side portion 1F and the back-side portion 1B may be fused together, thereby producing the ring-shaped fitting portion 1. While the fitting portion 1 is shown to be in an endless and ring-shaped form in the embodiment of FIGS. 6(a) and 6(b), the fitting portion 1 does not need to be in a ring-shaped form and does not need to be in an endless form.

The elastic member 12 is only required to be provided at least in an part of the fitting portion 1. For example, there may be no elastic member 12 in a portion of the fitting portion 1 that is overlapped with the absorbent portion 2. Such a structure helps preventing the thick absorbent portion 2 from giving stiff feel, and thus improves the wearability.

The absorbent portion 2 includes a topsheet 20, a core 21 and a backsheet 22. The absorbent portion 2 may further include a second sheet between the topsheet 20 and the core 21. The topsheet 20 is permeable to body fluid of the wearer, e.g., urine or blood. The topsheet 20 or the second sheet may have a function of preventing a reverse flow of body fluid. Thus, while body fluid can flow from the topsheet 20 into the core 21, it hardly flows in the reverse direction.

The core 21 is capable of absorbing and holding body fluid. The core 21 may be, for example, fluff pulp obtained by fiberizing (crushing) pulp with a fiberizer (crusher) into a fibrous form, or a material obtained by mixing the fluff pulp with superabsorbent polymer particles (absorbent polymer) and letting it deposit into a cotton-like form. The core 21 has an absorptive property. Alternatively, an airlaid material may be used as the core 21 or as a portion of the core 21.

The backsheet 22 is impermeable to fluid. The backsheet 22 may be a polyethylene sheet, or the like.

A first end portion (one end) 23 of the absorbent portion 2 of FIG. 1(a) is detachably joined to a first area 13 of the abdominal-side portion 1F of the fitting portion 1 via detachable fastener members 3, and a second end portion (the other end) 24 of the absorbent portion 2 is joined to a second area 14 of the back-side portion 1B of the fitting portion 1.

The detachable fastener members 3 may each be a touch fastener, an adhesive tape, or the like. The fastener members 3 are provided on the first area 13 of the fitting portion 1 or the first end portion 23 of the absorbent portion 2. For example, a male hook and loop fastener or a female hook and loop fastener may be secured on the fitting portion 1, with a female hook and loop fastener or a male hook and loop fastener being secured on the absorbent portion 2.

As one surface of the absorbent portion 2 and one surface of the fitting portion 1 are joined in face contact with each other in such a manner, the first end portion 23 of the absorbent portion 2 can be detached from the fitting portion 1.

The first end portion 23 may be joined to the second area 14 of the back-side portion 1B of the fitting portion 1, or the second end portion 24 may be joined to the first area 13 of the abdominal-side portion 1F of the fitting portion 1.

As shown in FIG. 1(a), a cover sheet 4 covers at least an area where the fitting portion 1 and the absorbent portion 2 overlap with each other, i.e., a joint area 5. In the example shown in FIG. 1, the cover sheet 4 covers generally the entire outer surface of the fitting portion 1. Therefore, the first end portion 23 of the absorbent portion 2 placed on the fitting portion 1 is also covered by the cover sheet 4. Thus, the cover sheet 4 covers an upper edge 2e of the first end portion 23 of the absorbent portion 2 on the fitting portion 1. The cover sheet 4 also covers the fastener members 3 provided on the fitting portion or the absorbent portion.

Thus, as the joint area 5 is covered by the cover sheet 4, it is possible to prevent the absorbent portion 2 from inadvertently coming off the fitting portion 1 in the joint area 5 while the article is being worn.

Referring to FIG. 2(a), while the absorbent portion 2 may be attached onto the inner side of the fitting portion 1, the absorbent portion 2 can be detached from the fitting portion 1 more easily when attached onto the outer side of the fitting portion 1. Thus, in the first end portion 23, it is preferred that the inner surface of the absorbent portion 2 faces the outer surface of the abdominal-side portion 1F of the fitting portion 1 via the fastener members 3 therebetween. Then, in the first end portion 23, it is more preferred that the inner surface of the cover sheet 4 faces the outer surface of the absorbent portion 2. Then, the fitting portion 1, the absorbent portion 2 and the cover sheet 4 are layered in this order starting from the inner side in a position corresponding to the first end portion 23. Thus, the first end portion 23 of the absorbent portion 2 is sandwiched between the fitting portion 1 and the cover sheet 4.

As shown in FIGS. 1(a) and 1(b), a tearable portion 41 is provided in the cover sheet 4. Specifically, a portion of the cover sheet 4 that is covering the first end portion 23 and/or the vicinity thereof is processed so that the cover sheet 4 is breakable. The tearable portion 41 may be formed, for example, by half cutting or making perforations. Tearing the cover sheet 4 along the tearable portion 41 will expose the absorbent portion 2 of the joint area 5, i.e., the first end portion 23 of the absorbent portion 2, as shown in FIG. 1(b). Thus, the fitting portion 1 and the absorbent portion 2 can be easily disconnected from each other. Moreover, the fitting portion 1 and the absorbent portion 2 can be easily reconnected to each other. The tearable portion 41 may be in a T-shaped pattern as shown in FIG. 2(*b*), an I-shaped pattern as shown in FIG. 2(*c*), or a pattern including two vertical lines as shown in FIG. 2(*d*).

As shown in FIG. 1(*b*), fastener members 7 are provided on the reverse surface of the cover sheet 4. Thus, after the cover sheet 4 is torn, the cover sheet 4 can be refastened to the fitting portion 1 via the fastener members 7. The arrangement of the tearable portion 41 and the fastener members 7 may be any of those shown in FIGS. 5(*a*) to 5(*f*).

SECOND EMBODIMENT

Figure 3A:
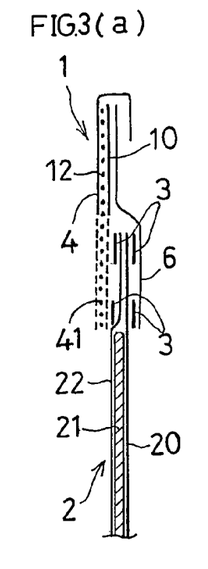
FIG. 3(a) is a schematic cross-sectional view showing an important part of a diaper of the second embodiment taken along line IIIa-IIIa.
Figure 3B:
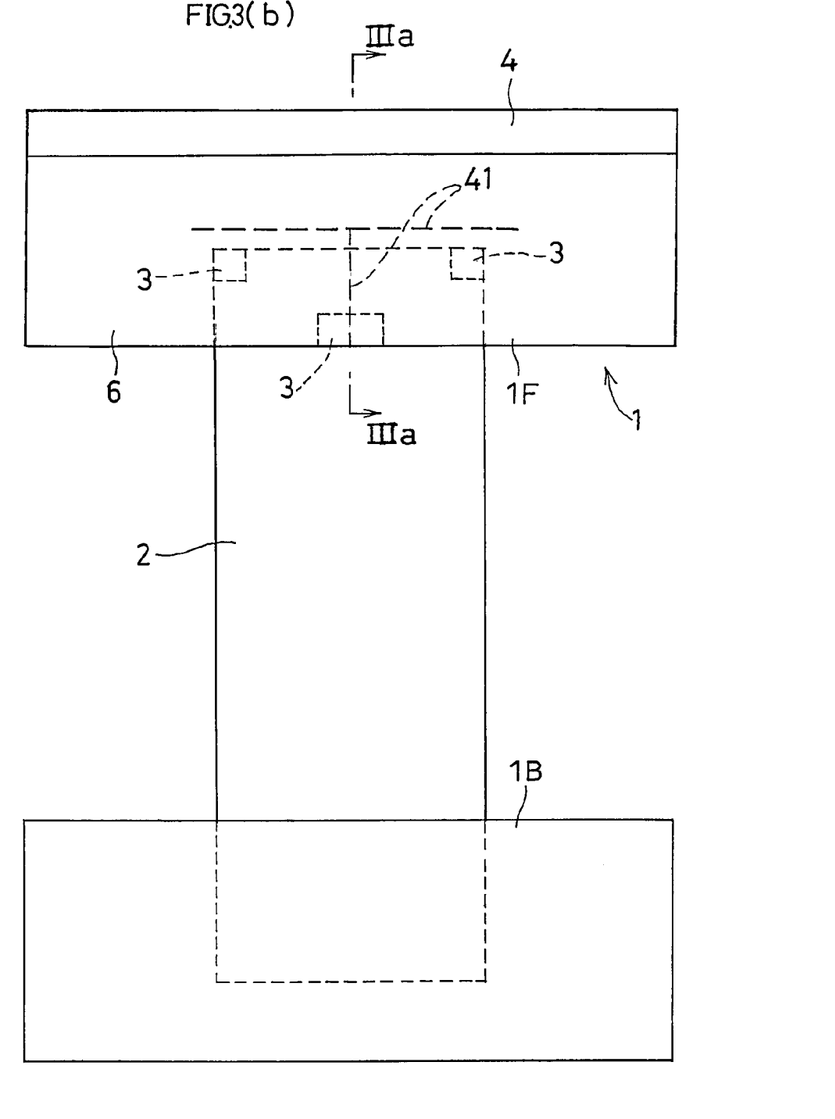
FIG. 3(b) is a plan view showing the diaper being spread out.

FIGS. 3(*a*) and 3(*b*) show the second embodiment.

The worn article of the second embodiment is a disposable diaper including the fitting portion 1, the absorbent portion 2, the fastener member 3 and a hold-down sheet 6. In the second embodiment, the cover sheet 4 together with the non-woven fabric 10 sandwiches the elastic members 12 therebetween. The hold-down sheet 6 is placed on the side to be in contact with the surface of the body of the wearer, and covers a portion of the absorbent portion 2 and part or whole of the non-woven fabric 10.

In the second embodiment, the tearable portion 41 is provided in the fitting portion 1. Specifically, the tearable portion 41 is formed in the cover sheet 4, the non-woven fabric 10 and the elastic members 12 of the fitting portion 1. In the tearable portion 41, the elastic members 12 are cut or cuttable.

To achieve such a state, the fitting portion 1 is embossed. The embossing process is performed by applying heat, pressure, or both heat and pressure to the elastic member 12 of the fitting portion 1 while the fitting portion 1 is sandwiched between an embossing roll having a plurality of protrusions thereon and an anvil roll. Alternatively, the elastic member 12 may be cut or made cuttable through irradiation of laser light, or the like.

Alternatively, no elastic member 12 may be provided in the position of the breakable portion 41 so that the breakable portion 41 can be broken.

The fastener members 3 may be placed on the inner side and/or the outer side of the absorbent portion 2. Thus, the fastening with the fastener members 3 may be done on the inner side of the absorbent portion 2, on the outer side of the absorbent portion 2, or both on the inner side and on the outer side of the absorbent portion 2. Particularly, if the fitting portion 1 and the absorbent portion 2 are fastened together via the fastener members 3, the absorbent portion 2 is unlikely to move with respect to the fitting portion 1, whereby the worn article can be worn by the wearer in a stable state. The fastener members 3 may be placed on the inner side of the fitting portion 1, instead of placing the fastener members 3 on the outer side of the absorbent portion 2.

In a case where the worn article can be worn by the wearer by fastening the hold-down sheet 6 and the absorbent portion 2 together, it is not always necessary to fasten the fitting portion 1 and the absorbent portion 2 together via the fastener members 3.

Third Embodiment

Figure 4:
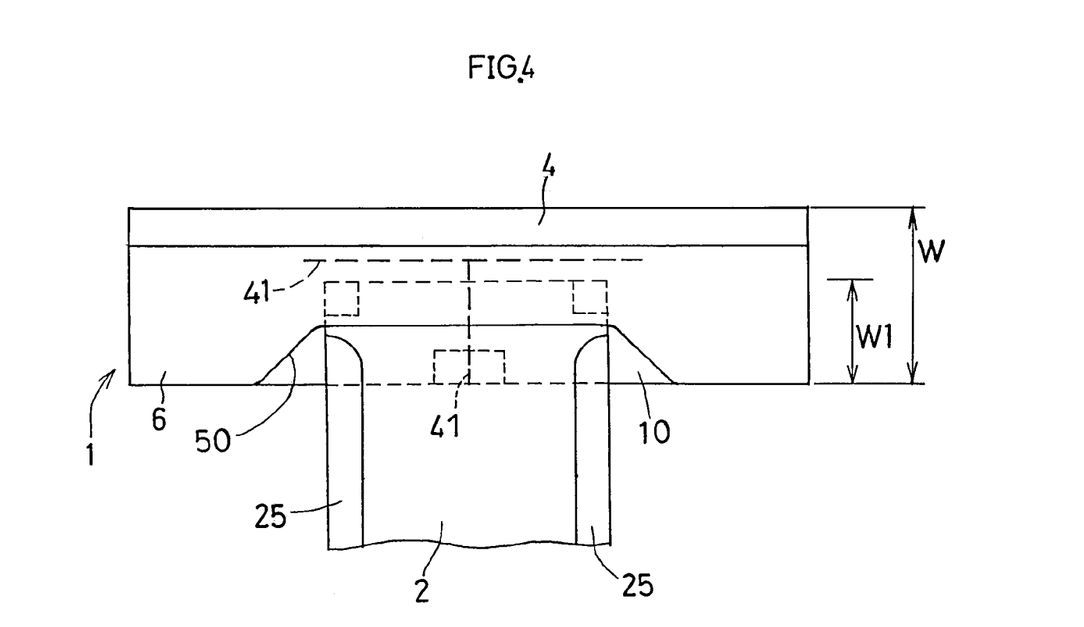
FIG. 4 is a schematic plan view showing an important part of a diaper of the third embodiment.
Figure 5:
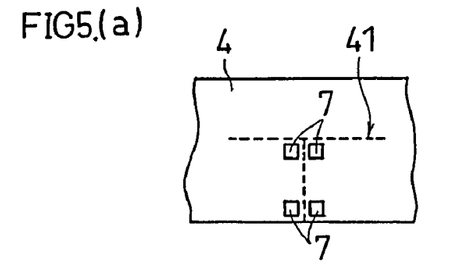
FIGS. 5(a) to 5(f) are plan views each showing an arrangement of the tearable portion and the fastener member in the first embodiment.

FIG. 4 shows an important part of the third embodiment.

The absorbent portion 2 may include a cuff 25. Then, a notch 50 may be formed by cutting a predetermined shape off a central portion of the hold-down sheet 6 as shown in FIG. 4. As a central portion of the hold-down sheet 6 is cut off, a portion of the absorbent portion 2 on the fitting portion 1 is not covered by the hold-down sheet 6. Therefore, almost all the surface of the absorbent body can be brought into direct contact with the wearer, whereby it is possible to sufficiently bring out the absorbing capability of the absorbent body. Even in the absorbent portion 2 near the fitting portion 1, the cuff 25 gives an anti-leak effect.

It is preferred that the width W1 over which the fitting portion 1 and the absorbent portion 2 overlap with each other is about ⅕ to about ⅘ of the width W of the fitting portion 1. Even in a case where the width W1 over which the fitting portion 1 and the absorbent portion 2 overlap with each other exceeds ½ of the width W of the fitting portion 1, if a central portion of the hold-down sheet 6 is cut off, almost all the surface of the absorbent body can be brought into direct contact with the wearer, whereby it is possible to sufficiently bring out the absorbing capability of the absorbent body. Moreover, the anti-leak effect of the cuff 25 of the absorbent portion 2 will not deteriorate.

Fourth Embodiment

Figure 9A:
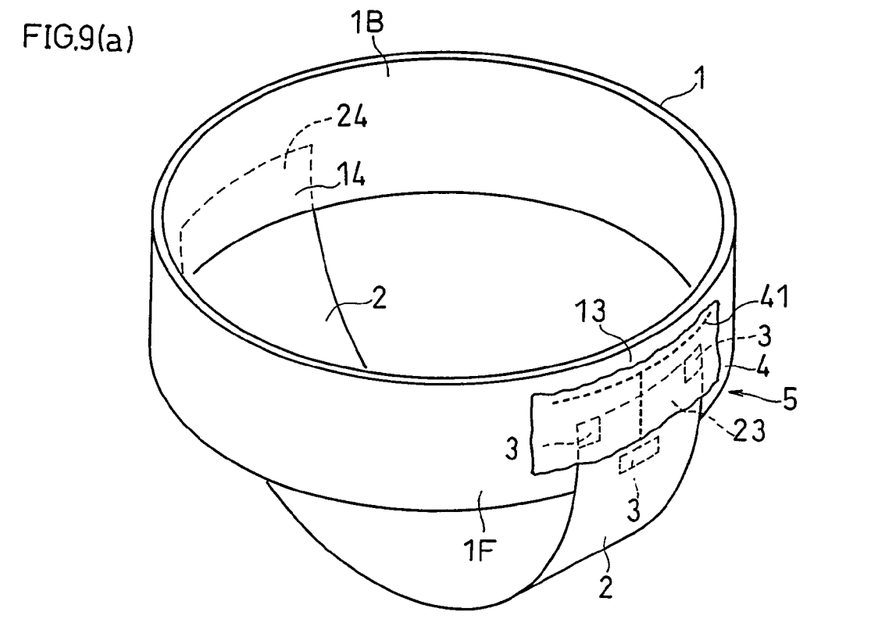
FIG. 9(a) is a schematic perspective view showing the worn article of the fourth embodiment.
Figure 9B:
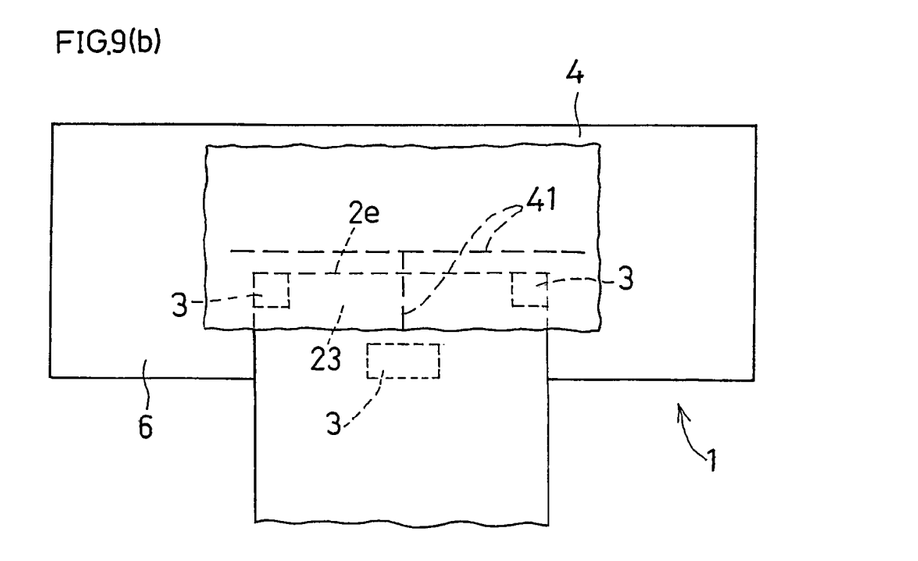
FIG. 9(b) is a partial plan view showing the worn article being spread out.

FIGS. 9(*a*) and 9(*b*) show the fourth embodiment.

In the present embodiment, the cover sheet 4 having the tearable portion 41 is provided only on the side of the abdominal-side portion IF, but not on the side of the back-side portion 1B. The cover sheet 4 does not cover the entire joint area 5 where the fitting portion 1 and the absorbent portion 2 are connected, but covers only a portion of the joint area 5. Specifically, the cover sheet 4 is provided so as to cover only a portion of the first end portion 23 of the absorbent portion 2 and the vicinity thereof. If the cover sheet 4 is formed in a small size as described above, it is possible to reduce the amount of material needed and thus to cut down the cost. The cover sheet 4 may be in such a size that it covers only the upper edge 2*e* of the first end portion 23 and the vicinity thereof.

The edge of the cover sheet 4 is fused onto the fitting portion 1. The fusion may be such that the wearer can peel the cover sheet 4 off the fitting portion 1 when tearing the tearable portion 41. Then, the wearer can peel off, and discard, the cover sheet 4. In such a case, there may be no tearable portion 41 provided. That is, the wearer can peel off the cover sheet 4, without tearing it.

While the cover sheet 4 may be formed in a small size as described above, it may alternatively be formed in such a size that it will protrude from the lower edge or the upper edge of the fitting portion 1.

Production Method

Now, a method for producing a worn article will be described.

Figure 7:
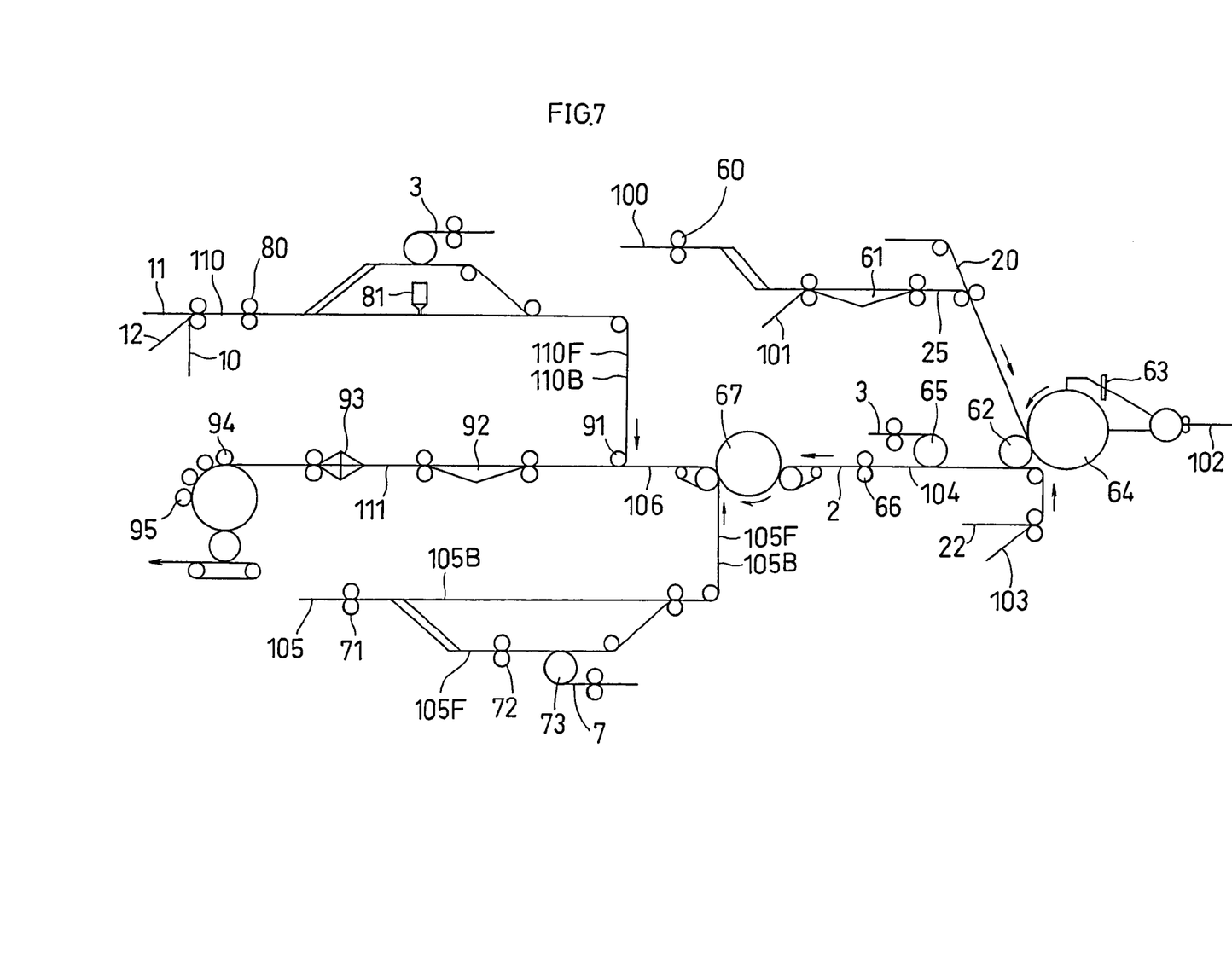
FIG. 7 is a schematic configuration diagram showing an apparatus for producing the worn article of FIG. 2(a).

FIG. 7 shows an apparatus for producing a worn article of FIG. 2(*a*).

First, a method for producing the absorbent portion 2 will be described.

As shown in FIG. 7, a non-woven fabric 100 is divided into two by a slitter 60. After a thread rubber 101 is placed on each piece of the divided non-woven fabric 100, each piece of the non-woven fabric 100 is folded back by a three-dimensional fold-back section (sailor) 61 to form the cuff 25. The cuff 25 is placed on the topsheet 20, and then the topsheet 20 is carried toward a drum 62.

On the other hand, a roll pulp 102 is milled (crushed) and fiberized by a mill (crusher) 63 to produce fluff. The fluff is layered on a pattern drum 64 to form a laminate. The laminate is placed on the topsheet 20 on the drum 62. The laminate is further sandwiched between the backsheet 22 having a thread rubber 103 for leg gathers and the topsheet 20. Then, small cut-off pieces of the fastener member 3 on a roll 65 are bonded onto the topsheet 20 to form a continuous member 104.

The continuous member 104 is cut by a cutter 66 into pieces of a predetermined size to produce many absorbent portions 2. The absorbent portions 2 are supplied to a re-pitching/turning turn drum 67.

Now, a method for producing the cover sheet 4 will be described.

A whole cloth sheet (resin film) 105 is divided into two sheets 105F and 105B by a slitter 71. The tearable portion 41 is formed by a die cutter 72 in the sheet 105F, one of the two sheets 105F and 105B that is to be the sheet to cover the abdominal-side portion 1F. Moreover, small cut-off pieces of the fastener member 7 on a roll 73 are bonded onto the sheet 105F.

Figure 10A:
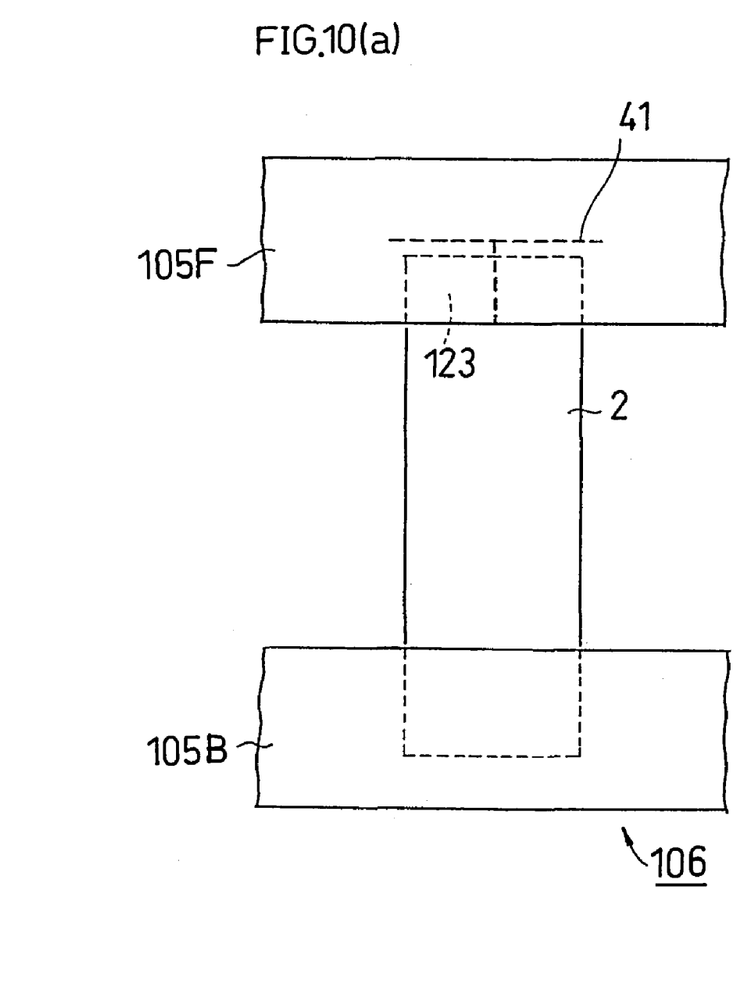
FIGS. 10(a) and 10(b) are schematic plan views showing steps of producing the worn article of FIG. 2(a).

Then, the sheets 105F and 105B are carried toward the re-pitching/turning drum 67 in a parallel arrangement. On the drum 67, the absorbent portion 2 is placed onto the pair of sheets 105F and 105B so that the absorbent portion 2 bridges therebetween, thereby producing a combined member 106 (FIG. 10(a)). An end portion 123 of the absorbent portion 2 that is to be the first end portion 23 is covered by the tearable portion 41 of the sheet 105F and the vicinity thereof.

Now, a method for producing the fitting portion will be described.

The elastic member 12 is sandwiched between the two sheets of non-woven fabric 10 and 11 to produce a laminate (web) 110. The laminate 110 is divided into two laminates 110F and 110B by a slitter 80. Small cut-off pieces of the fastener member 3 are bonded onto the laminate 110F to be the abdominal-side portion 1F. An adhesive is applied from an applicator 81 onto the laminate 110B to be the back-side portion 1B. The laminates 110F and 110B are carried toward a roller 91 downstream of the re-pitching/turning drum 67 in a parallel arrangement.

Now, the step of producing the article from the various members will be described.

Figure 10B:
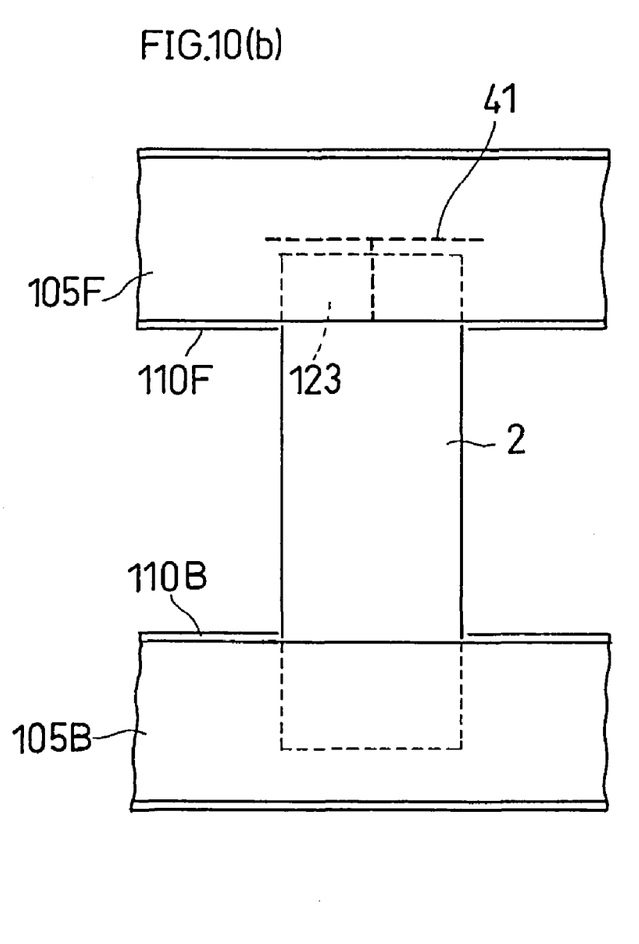

The combined member 106 is carried toward the roller 91, and the laminates 110F and 110B are placed onto the sheets 105F and 105B, respectively (FIG. 10(b)). The laminates 110F and 110B are laid on one side of the sheets 105F and 105B on which the absorbent portion 2 is placed. The laminates 110F and 110B are placed so that the absorbent portion 2 bridges between the laminates 110F and 110B. Then, the end portion 123 of the absorbent portion 2 that is to be the first end portion 23 is laid on the laminate 110F Thus, the end portion 123 of the absorbent portion 2 is sandwiched between the laminate 110F and the sheet 105F.

Then, a portion of the sheets 105F and 105B is folded back by a waist fold-back section (sailor) 92. A sheet-like member 111 to be the worn article is folded in two by a two-fold folding device 93, and then fused by a heat seal 94 along a portion to be the end portion of each worn article. Then, the sheet-like member 111 is cut into individual articles by an article cutter 95. Thus, the worn article of FIG. 2(a) is produced.

Now, another method for producing a worn article will be described.

Figure 8:
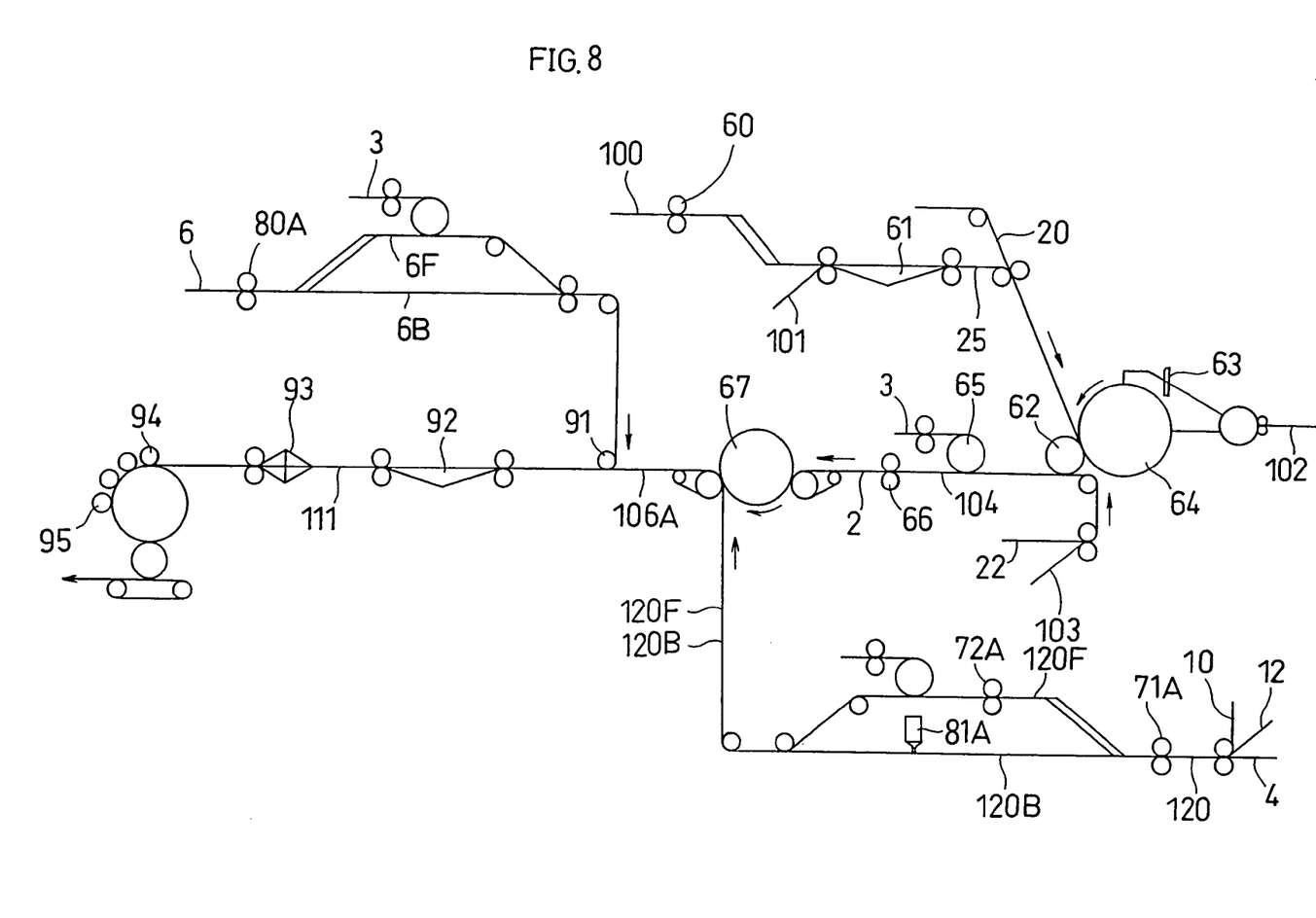
FIG. 8 is a schematic configuration diagram showing an apparatus for producing the worn article of FIG. 3(a).

FIG. 8 shows an apparatus for producing a worn article of FIG. 3(a).

As shown in FIG. 8, the cover sheet 4 is layered together with the non-woven fabric 10 with the elastic member 12 being inserted therebetween. Thus, a laminate 120 is produced. The laminate 120 is divided into two laminates 120F and 120B by a slitter 71A. The tearable portion 41 of a predetermined shape is formed by heating means 72A in the laminate 120F, one of the laminates 120F and 120B that is to be the abdominal-side portion 1F. Then, small cut-off pieces of the fastener member 3 are bonded onto the laminate 120F. An adhesive is applied from an applicator 81A onto the laminate 120B, one of the laminates 120F and 120B that is to be the back-side portion 1B.

The absorbent portion 2 on the re-pitching/turning drum 67 is placed onto the laminates 120F and 120B. Thus, a combined member 106A is produced, and carried toward the roller 91.

On the other hand, the hold-down sheet 6 is divided into two hold-down sheets 6F and 6B by a slitter 80A. Then, small cut-off pieces of the fastener member 3 are bonded onto the hold-down sheet 6F of the hold-down sheet 6 that is to be part of the abdominal-side portion 1F. The two hold-down sheets 6F and 6B are carried toward the roller 91.

The pair of hold-down sheets 6F and 6B on the roller 91 are layered together with the pair of laminates 120F and 120B of the combined member 106A.

The method is otherwise similar to that of FIG. 7, and will not be further described below while giving the same reference numerals to the same or corresponding elements.

While preferred embodiments of the present invention have been described above with reference to the drawings, obvious variations and modifications will readily occur to those skilled in the art upon reading the present specification.

For example, both ends of the absorbent portion may be detachably fastened to the fitting portion, with one or both of the joint areas being covered by the cover sheet.

The cover sheet may be provided only in the joint area, or may be provided only in one of the abdominal-side portion and the back-side portion, covering the joint area.

For example, as disclosed in Japanese National Phase PCT Laid-Open Publication No. 2003-520627 (abstract), the member forming the abdominal-side portion or the back-side portion of the fitting portion may cover substantially the entire absorbent body in a state where the worn article being spread out. The member forming the abdominal-side portion may be formed so as to extend to the back-side portion, or the member forming the back-side portion may be formed so as to extend to the abdominal-side portion.

Thus, such variations and modifications shall fall within the scope of the present invention as defined by the appended claims.

INDUSTRIAL APPLICABILITY

The present invention is applicable to disposable diapers and disposable pants.

The invention claimed is:

1. A worn article, comprising a fitting portion for fitting around a torso of a wearer and including an elastic member sandwiched between two sheets of nonwoven fabric, and an absorbent portion for covering a crotch of the wearer and absorbing body fluid from the wearer, wherein:
    the absorbent portion includes a first end portion and a second end portion that are connected to the fitting portion;
    the first end portion of the absorbent portion is detachable from the fitting portion;
    the fitting portion includes an abdominal-side portion adapted for covering an abdominal side of the wearer, and a back-side portion adapted for covering a back side of the wearer;
    the first end portion of the absorbent portion is connected to the abdominal-side portion of the fitting portion, and the second end portion of the absorbent portion is connected to the back-side portion of the fitting portion;

the first end portion is detachably touch-fastened to the abdominal-side portion of the fitting portion; and a cover sheet covers at least a portion of an exterior surface of the first end portion which is opposite to a surface facing the skin surface of the wearer, an upper edge of the first end portion extending in a torso direction, and at least a portion of an outer surface, to which the first end portion is touch-fastened, of the abdominal-side portion of the fitting portion during wearing;

wherein, when the article is worn, the cover sheet is at least partially removable to expose the exterior surface of the first end portion of the absorbent portion to an exterior of the worn article for detaching the absorbent portion from the fitting portion;

a portion of the cover sheet that is covering the first end portion or a vicinity thereof is tearable and comprises perforations;

in the touch-fastened first end portion, an inner surface of the absorbent portion is facing the outer surface of the abdominal-side portion of the fitting portion, and an inner surface of the cover sheet is facing an outer surface of the absorbent portion; and the fitting portion, the absorbent portion and the cover sheet are layered in this order starting from an inner side in a position corresponding to the first end portion.

2. A worn article according to claim 1, wherein:

the cover sheet is processed so that the cover sheet is tearable; and a fastener member for detachably fastening together the absorbent portion and the fitting portion is placed on the absorbent portion or the fitting portion in a vicinity of the processed portion of the cover sheet.

3. A worn article according to claim 1, wherein a tearable portion for tearing the cover sheet is formed in the cover sheet by processing the cover sheet so that at least a portion of the first end portion of the absorbent portion will be exposed to an exterior of the article when the cover sheet is torn along the tearable portion.

4. A worn article according to claim 1, wherein the cover sheet covers at least an upper edge of the first end portion of the absorbent portion.

5. A method for producing a worn article according to claim 1, wherein a member forming the absorbent portion and the cover sheet are placed on a web forming the fitting portion while carrying the web, the method comprising the steps of:

processing a portion of the cover sheet to be tearable;

carrying the web in a longitudinal direction of the web;

placing the member forming the absorbent portion on the web so that the member overlaps at least a portion of the web; and placing the member forming the absorbent portion on the cover sheet so that the member overlaps at least a portion of the cover sheet processed to be tearable, wherein the member forming the absorbent portion is sandwiched between the cover sheet processed to be tearable and the web as a result of carrying out the above steps.

6. A worn article according to claim 1, wherein:

a tearable portion processed for tearing the cover sheet is formed in the cover sheet, a member for fastening is provided to the inner surface of the cover sheet, and to one of the outer surface of the abdominal-portion of the fitting portion and the outer surface of the absorbent portion so that the inner surface of the cover sheet comes off from the outer surface of the abdominal-side portion of the fitting portion and the outer surface of the absorbent portion, and the inner surface of the cover sheet is detachably touch-fastened to the outer surface of the abdominal-side portion of the fitting portion and the outer surface of the absorbent portion.

7. A worn article according to claim 1, wherein:

the first end portion has a side edge that is in vicinity to the upper edge and that extends in a vertical direction, the cover sheet covers the side edge of the first end portion, and the cover sheet also covers an entirety of the upper edge of the first end portion.

8. A worn article according to claim 2, wherein:

the first end portion has a side edge that is in vicinity to the upper edge and that extends in a vertical direction, the cover sheet covers the side edge of the first end portion, and the cover sheet also covers an entirety of the upper edge of the first end portion.

9. A worn article according to claim 6, wherein:

the first end portion has a side edge that is in vicinity to the upper edge and that extends in a vertical direction, the cover sheet covers the side edge of the first end portion, and the cover sheet also covers an entirety of the upper edge of the first end portion.

\* \* \* \* \*